United States Patent [19]
Muehlemann

[11] Patent Number: 5,752,767
[45] Date of Patent: May 19, 1998

[54] DIFFUSE RING ILLUMINATOR

[75] Inventor: Michael Mark Muehlemann, Liverpool, N.Y.

[73] Assignee: Illumination Technologies Inc., East Syracuse, N.Y.

[21] Appl. No.: 548,488

[22] Filed: Oct. 26, 1995

[51] Int. Cl.⁶ .................................................. F21V 7/00
[52] U.S. Cl. .......................... 362/277; 362/280; 362/319; 362/346
[58] Field of Search ......................... 362/32, 277, 280, 362/319, 297, 346, 321; 359/387, 599; 356/446

[56] References Cited

U.S. PATENT DOCUMENTS

| | | |
|---|---|---|
| 1,444,400 | 2/1923 | Silverman . |
| 1,873,149 | 8/1932 | Perez . |
| 4,160,578 | 7/1979 | Gottlieb et al. ............... 350/89 |
| 5,179,474 | 1/1993 | Bailey et al. ............... 359/798 |
| 5,268,749 | 12/1993 | Weber et al. ............... 356/446 |

FOREIGN PATENT DOCUMENTS

| | | | |
|---|---|---|---|
| 3100662 | 11/1981 | Germany ............... | 359/387 |
| 0155106 | 6/1990 | Japan ............... | 359/599 |

*Primary Examiner*—Y. My Quach
*Attorney, Agent, or Firm*—Trapani & Molldrem

[57] ABSTRACT

A diffuse illuminator device is disclosed for providing uniform illumination onto a target. A generally tubular outer baffle, which has a proximal and an open distal end, defines an optic axis. A generally tubular inner baffle which is open at its proximal and distal ends is coaxially disposed within the outer baffle. An annular illuminator, positioned at the proximal end of the outer and inner baffles, directs a ring of illumination into an annular light tunnel which is defined by the space between the inner and outer baffles. This arrangement allows viewing of the target through the inner baffle. The inner baffle may also be adjusted along the optic axis in order to vary the illumination structure of the light on the target.

20 Claims, 5 Drawing Sheets

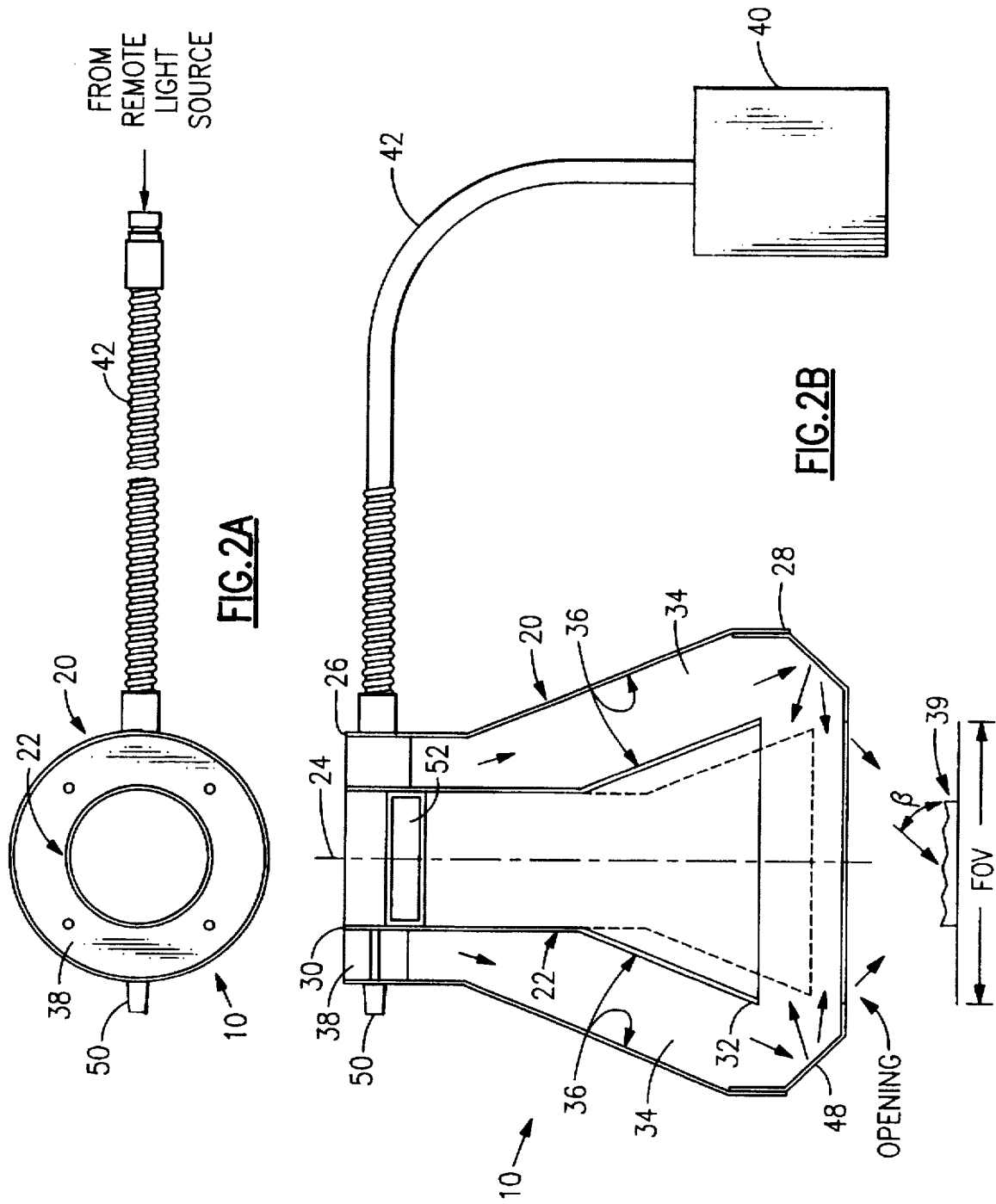

DIFFUSE RING ILLUMINATOR

BACKGROUND OF THE INVENTION

This invention relates to illuminating devices and more particularly to illuminating devices for providing uniform illumination of a target. The invention is specifically concerned with those illuminating devices capable of providing a full 360 degrees of shadow-free and glare-free illumination.

Many attempts have been made in the past to provide highly uniform and diffuse illumination of targets, especially those which are flat and specularly reflective. When such targets are viewed through a lens or photographed, they are very difficult to image accurately. One attempt to alleviate this problem has been to radiate light onto the target from above. This technique however, often results in a shadow at the bottom of the target. The use of shade rings has been unsuccessfully employed to reduce the shadowing affect. In other instances, a light flux is introduced into a chamber containing both diffuse and specular surfaces, and reflected towards the target. These devices however fail to provide a full range of uniform illumination. Furthermore, when a target is viewed through a lens, it produces an effect known as lens roll-off. This results from the non-uniformity of the transfer function across the diameter of the lens. Consequently, the amount of light passing through the lens decreases from the center to the edge of the lens. The resulting image is bright at the center and dim along the edges. None of the previous designs have been able to compensate for camera lens roll-off. Accordingly, an illuminating device would be beneficial for providing shadow-free illumination of a target while being able to compensate for optical anomalies.

Several designs have been proposed by the prior art to eliminate the problems associated with the imaging of targets. For example, U.S. Pat. No. 5,268,749 shows an apparatus for uniformly illuminating a sample plane. The apparatus is designed to provide ±45° conical illumination in compliance with standards set forth by the American National Standards Institute (ANSI). A lamp is used to provide a light flux which enters an integrating chamber where it is homogenized and emitted through an exit port. The interior of the chamber is treated so that it contains both reflective and diffusive surfaces. An annular stop placed between the exit port and an imaging optic prevents errant, non-conforming light from reaching the imaging optic. An optical receptor, located within the imaging optic, collects the light reflected from the sample. The apparatus is only suitable for 45° conical homogenization of light with a 5° tolerance. Furthermore only optical fiber imagers or similarly small devices are suitable for viewing the sample being illuminated.

U.S. Pat. No. 5,179,474 shows an illuminating device for the viewing system of object sorting machines. The apparatus includes a housing illuminated by an internal light source. A number of viewing devices are mounted in the housing. The objects to be sorted move through a transparent window within the housing and are viewed against a background member. A shade ring prevents direct light from entering the viewing devices, while a top and bottom mirror reflect light to areas which would otherwise be dark. Although mirrors are provided to further illuminate certain areas, there is no precise way to control the angle at which light is projected towards the surface.

U.S. Pat. No. 4,160,578 describes an illuminating device for a microscope objective. The device includes a reflector positioned at the bottom of an annular light path. When using the device however, the radius of the reflecting surface must be in a specific relationship to the microscope objective in order to uniformly distribute light onto the object surface.

U.S. Pat. No. 1,873,149 shows an apparatus for examining pictures with lateral lighting. The apparatus includes a casing which has an upper and lower face and a tube which contains a lenticular system. Both the upper and lower face contain a central opening. A pair of lamps located above the target provides the illumination. Two mirrors one of each associated with a lamp is used to reflect the light towards the central opening for illumination of the object to be examined. However, the use of multiple light sources decreases the uniformity of the illumination.

U.S. Pat. No. 1,444,400 shows an illuminator for optical instruments. The illuminator contains a ring light source, an inner shield and an outer shield, with a viewing instrument sighting through the center of the inner shield. Light travels through an annular cavity between the shields, and diffuses at the bottom. The surfaces of the cavity can be polished, white, or matte. However, the inner baffle is incapable of adjustment along the optic axis in order to change the illumination pattern. Also, the illuminator is specifically constructed for a microscope objective or a magnifier, and hence is of quite small dimensions.

While the foregoing arrangements address the need for imaging devices capable of uniformly illuminating a target, the problem persists. Most of the prior art focuses on arrangements suitable only for use with a microscope. Others are unable to adequately eliminate shadowing. Consequently, it remains difficult to obtain a full 360° of shadow-free, and glare-free illumination.

OBJECTS AND SUMMARY OF THE INVENTION

Accordingly, it is an object of this invention to provide an illuminating device which avoids the problems of the prior art.

It is another object of this invention to provide an illuminating device capable of providing uniform illumination of a target.

It is yet another object of this invention to provide an illuminating device capable of providing a full 360° of shadow free and glare free illumination.

It is yet another object of this invention to provide an illuminating device capable of being adjusted in order to vary the illumination pattern.

It is a further object of this invention to provide an illuminating device capable of compensating for camera lens roll-off.

In accordance with the objects of this invention, a diffuse illuminator device is provided to illuminate a target uniformly. The device consists of an outer baffle which is generally tubular and defines an optic axis. The outer baffle includes a proximal end and an open distal end. An inner baffle which is also generally tubular is coaxially located within the outer baffle. The proximal and distal ends of the inner baffle are also open. An annular light tunnel is formed from the space between the inner and outer baffles. The outer baffle also shields the target from the effects of ambient lighting.

An annular illuminator is positioned at the proximal end of the inner and outer baffles. The annular illuminator directs a ring of illumination into the annular light tunnel and permits viewing of the target through the inner baffle. In order to provide proper illumination of the target, the surfaces of the annular light tunnel are given specific optical qualities. Depending on the application, the surfaces can be diffuse, reflective, or light absorbent. A combination of these properties can also be used. The inner surface of the inner baffle can also be diffuse, reflective, or light absorbent in order to provide proper viewing of the target or to compensate for optical anomalies. An illumination structure is formed by the light emitted onto the target. The illumination structure is composed of light having various angles of incidence of the light on the target. In general, light having an angle of incidence greater than 45° is considered high angle, while light having an angle of incidence less than 45° is considered low angle. The term "illumination structure" as used in the description and in the claims means the relative mix of high angle and low angle light that is incident on the target.

It is also possible to adjust the position of the inner baffle along the optic axis with respect to the outer baffle. The illumination structure of the light can be varied by adjusting the inner baffle. In varying the illumination structure, the light incident on the target can be restricted to low angle or a combination of low angle and high angle. For example, the percentage of high angle light present in the illumination structure is reduced as the inner baffle is lowered. Consequently, light that is errant or otherwise non-conforming with the desired angles of incidence are restricted from reaching the target. The outer baffle can also be designed to terminate in an annular lip to further restrict errant light from the target. A beam splitter can also be placed in the inner baffle near the distal end in order to eliminate the reflection of the observer or imager when viewing the target.

In one embodiment of the invention, a remote light source is used to provide light to the annular illuminator. A light conduit which is connected to the remote light source conducts the light into the annular illuminator. The light conduit can be made of various materials including an optical fiber bundle. Light from the annular light tunnel may be directed at a low angle of incidence towards the target. This is accomplished by fitting an annular reflector within the distal end of the outer baffle. The annular reflector is angled so that it properly reflects the light.

In another embodiment of the invention, the outer baffle has a truncated conical shape having a major cross-sectional diameter at its distal end and minor cross-sectional diameter at its proximal end. The proximal end of the outer baffle terminates in a cylindrical extension. The inner baffle has a generally cylindrical proximal portion which is outwardly flanged to a distal portion having a cross-sectional diameter greater than the cross-sectional diameter of its proximal portion. The distal portion of the inner baffle may also contain a cross-sectional diameter which is greater than the minor cross-sectional diameter of the outer baffle. This particular arrangement restricts direct illumination of the target by the annular illuminator.

The inner and outer baffles can take a variety of shapes. For example, the cross-sectional areas of the inner and outer baffles do not have to be elliptical, or circular. The cross-sectional areas may be rectangular, triangular, pentagonal, etc., depending on the requirements of the specific application. Furthermore, the cross-sectional area of the inner and outer baffles may be asymmetric or non-uniform in instances where the illuminating device must be fitted within another apparatus. Thus, the term "annular" as used here to describe the spacing between the inner and outer baffles is not limited to circular shapes, but can be of any suitable shape, as disclosed.

The above and many other objects, features and advantages of this invention will be better understood from the ensuing description of selected preferred embodiments, which should be read in conjunction with the accompanying Drawing.

BRIEF DESCRIPTION OF THE DRAWING

FIG. 2A is a top plan view of the diffuse illuminator device of this embodiment;

FIG. 2B is a sectional view of a diffuse illuminator device of this embodiment.

DESCRIPTION OF THE PREFERRED EMBODIMENTS

Figure 1:
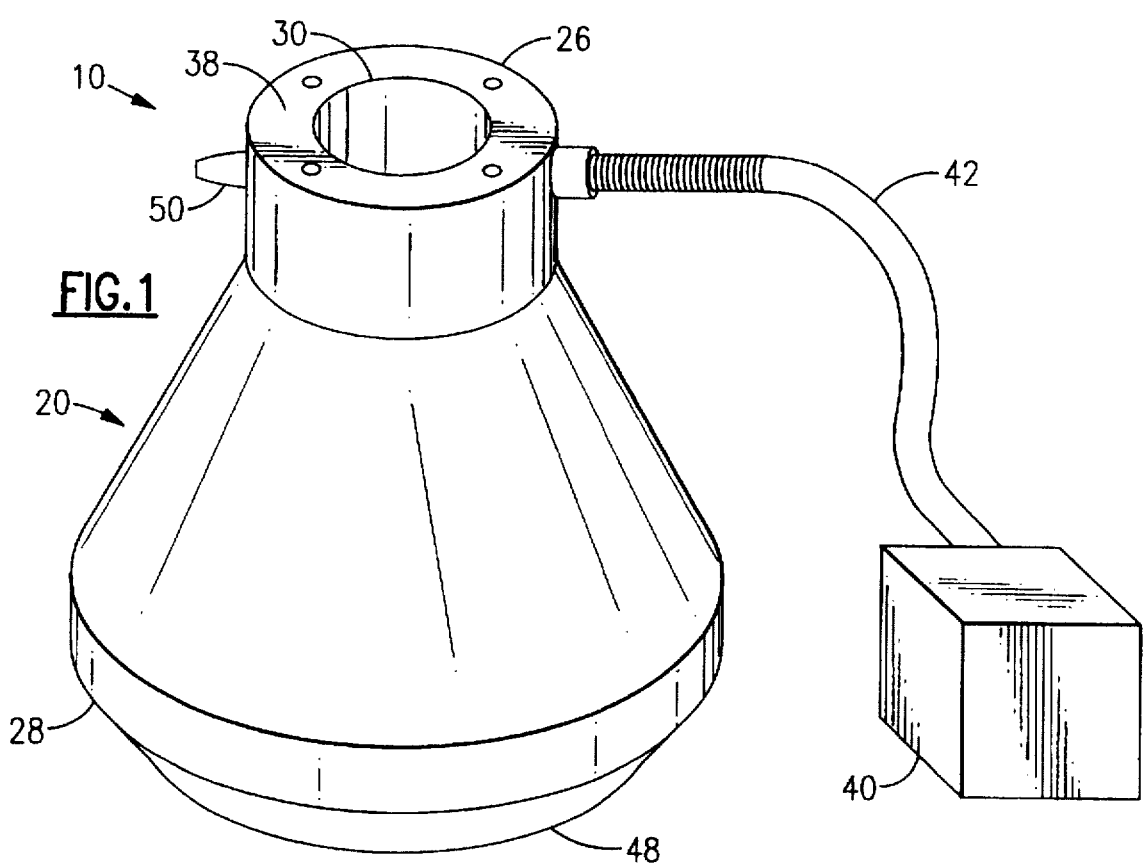
FIG. 1 is a perspective view of a diffuse illuminator device according to an embodiment of this invention.

With reference to the Drawing, and initially to FIGS. 1, 2A, and 2B, a diffuse illuminator device 10 has an outer baffle 20 and an inner baffle 22 which is coaxially disposed within the outer baffle 20. The outer baffle 20 defines an optic axis 24 and includes a proximal end 26 and an open distal end 28. The inner baffle 22 contains an open proximal end 30 and an open distal end 32. An annular light tunnel 34 is formed by the cavity contained between the outer baffle 20 and the inner baffle 22. The target 39 is viewed under an illumination structure having a combination of high and low angle light. Light incident on the target 39 at an angle greater than 45° is generally considered high angle while light incident on the target 39 at an angle less than 45° is considered low angle. When viewing a target 39, the inner baffle 22 shields the target 39 from high angle illumination. The outer baffle 20 shields the target 39 from the effects of ambient lighting which can sometimes produce erroneous features. As shown, the lower or distal end 32 of the inner baffle is free of any focusing lenses, and provides an unobstructed view to the target 39.

An annular illuminator 38 is positioned at the proximal ends 30, 26 of the inner and outer baffles 22, 20. A remote light source 40 introduces light into the annular illuminator 38 via a light conduit 42. The annular illuminator 38 directs a ring of illumination into the annular light tunnel 34 and onto the target. The surface 36 of the annular light tunnel 34 may be given specific optical qualities in order to provide proper illumination of the target 39. The surface 36 of the annular light tunnel 34 may be diffuse, reflective, or light absorbent. It is also possible to combine these properties on the various surfaces. The inner surface of the inner baffle 22 may also be diffuse, reflective, or light absorbent in order to provide proper viewing of the target 39 or to compensate for camera lens roll off.

As illustrated by the phantom lines, the inner baffle 22 is adjustable along the optic axis with respect to the outer baffle 20 in order to vary the illumination structure of the light. By varying the illumination structure, the angle of incidence β of light on the target 39 can be restricted to low angles or a combination of low and high angles. Thus, the target 39 can be properly illuminated regardless of its surface properties. Once the inner baffle 22 is adjusted, a set screw 50 or other means of securement holds it in place. The set screw 50 has a handle portion disposed outside the outer baffle 20. A beam splitter 52 is located near the proximal end of the inner baffle 22 for eliminating reflection of the observer.

The outer baffle 20 may also be fitted with an annular reflector 48 within the inner portion of its distal end 28. The annular reflector 48 is used to direct low angle illumination onto the target. The annular reflector may have a diffuse surface in the light tunnel. Alternatively, the annular reflector may have a specular surface in the light tunnel. The cross sectional area of the outer baffle 20 may take varying shapes, such as rectangular or triangular depending on the specific application. Also, the light conduit 42 which is used to conduct light from the remote light source 40 to the annular illuminator 38 may employ an optical fiber bundle.

The distal portions of the inner and outer baffles are outwardly flanged, and the annular tunnel 34 defined between them is likewise outwardly flanged. This construction, which ensures that light can only exit the light tunnel 34 if it is reflected first off at least one surface, is discussed in more detail below in respect to FIGS. 4A and 4B. The surface or surfaces in the light tunnel that direct low angle illumination can include at least one diffuse surface.

Figure 3A:
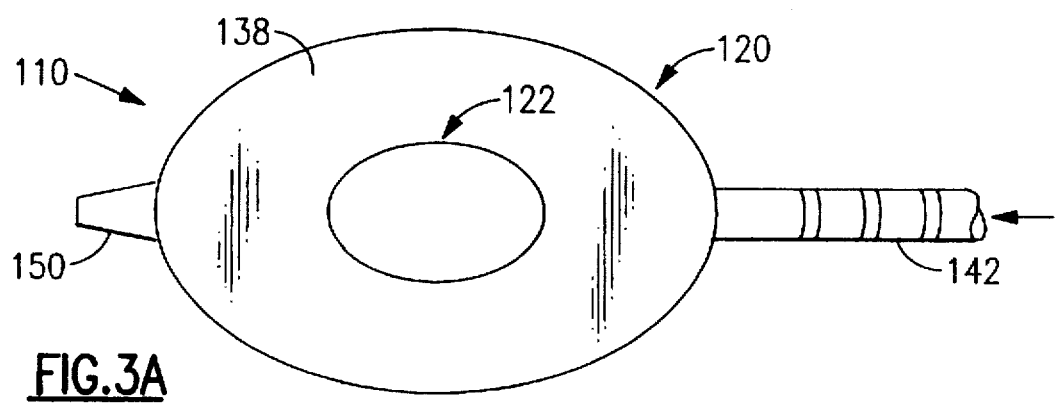
FIG. 3A is a top plan view of another embodiment of this invention in which the cross-sectional area of the outer baffle is elliptical.
Figure 3B:
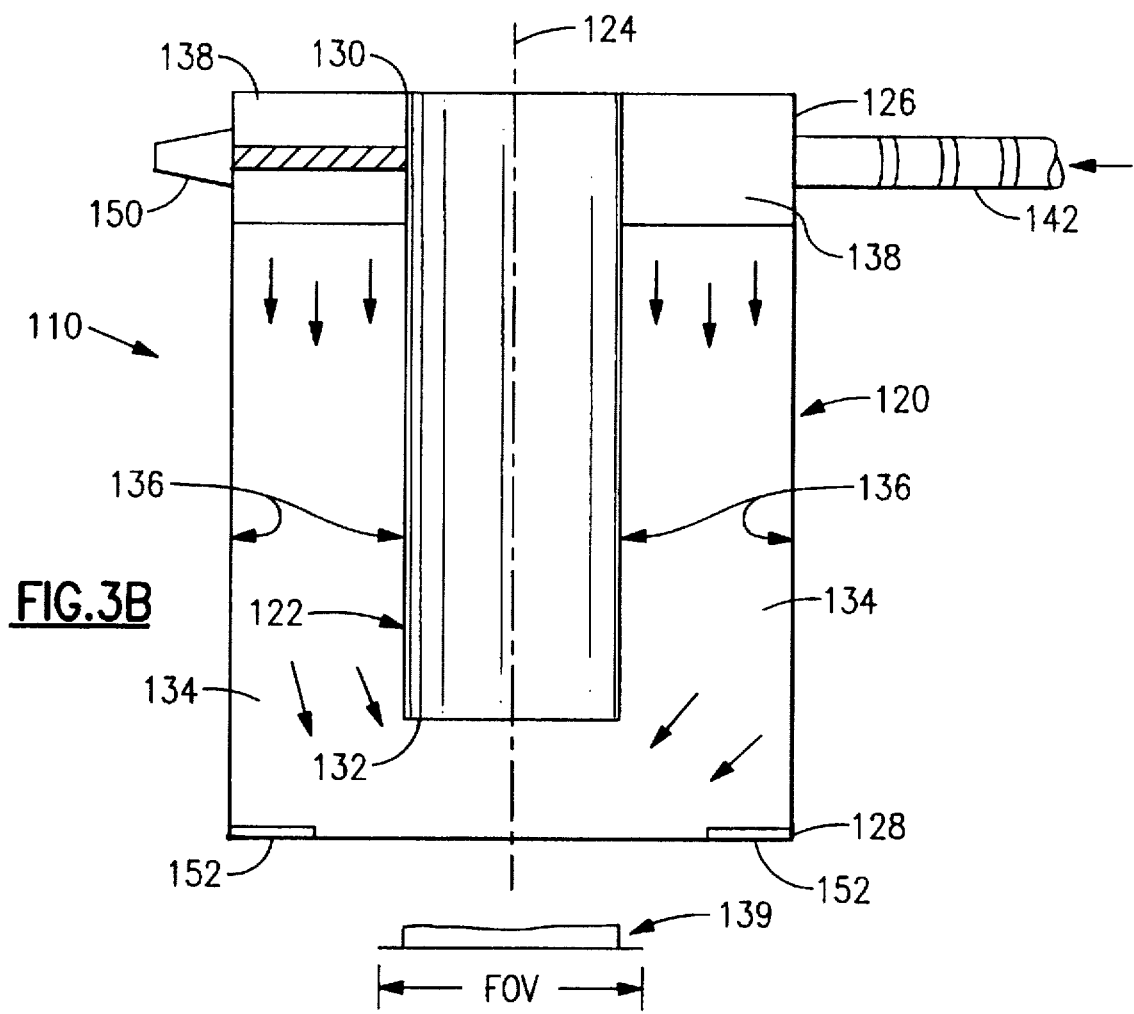
FIG. 3B is a sectional view of the same embodiment.

FIGS. 3A and 3B illustrate another embodiment of a diffuse illuminator device 110. The diffuse illuminator device 110 includes an outer baffle 120 having an elliptical cross sectional area. The outer baffle 120 has a proximal end 126 and an open distal end 128. The outer baffle 120 terminates in an annular lip 152 in order to restrict errant light from the target 139. An optic axis 124 is also defined by the outer baffle 120. An inner baffle 122 which also has an elliptical cross sectional area is shown coaxially disposed within the outer baffle 120. The inner baffle 122 includes an open proximal end 130 and an open distal end 132. An annular illuminator 138 is positioned at the proximal ends 130, 126 of the inner and outer baffles 122, 120. The annular illuminator 138 directs a ring of illumination towards the target. The inner baffle 122 is designed to prevent light from the annular illuminator 138 from being directly reflected onto the target 139. As seen in FIG. 3B, light is introduced into the annular illuminator via a light conduit 142. A set screw 150 is shown securing the inner baffle 122 to a selected position along the optic axis.

Figure 4A:
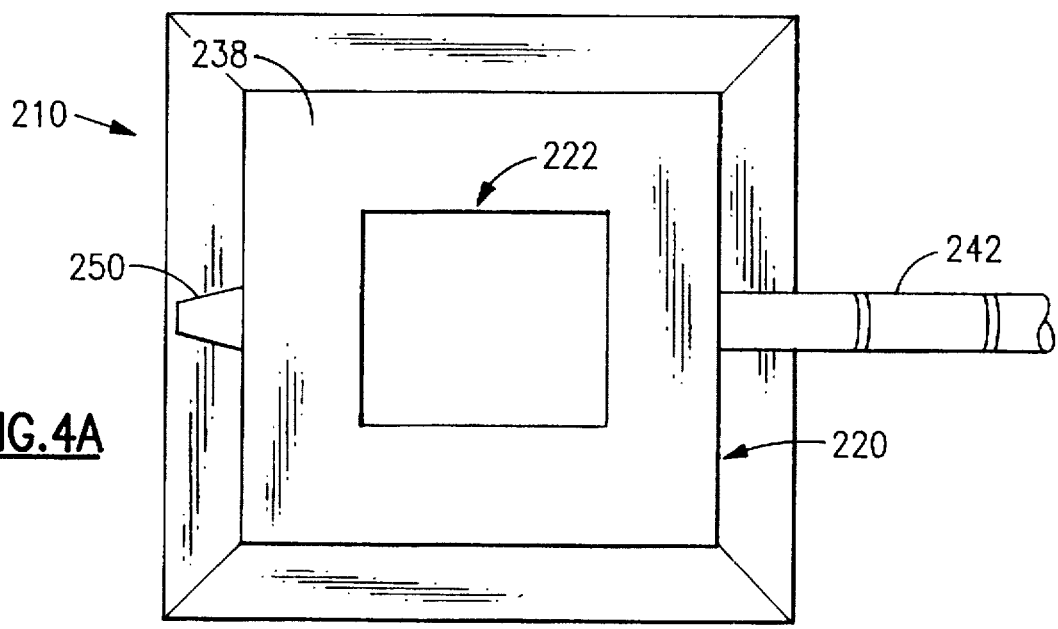
FIG. 4A is a top plan view of another embodiment of this invention in which the cross-sectional area of the outer baffle is rectangular.
Figure 4B:
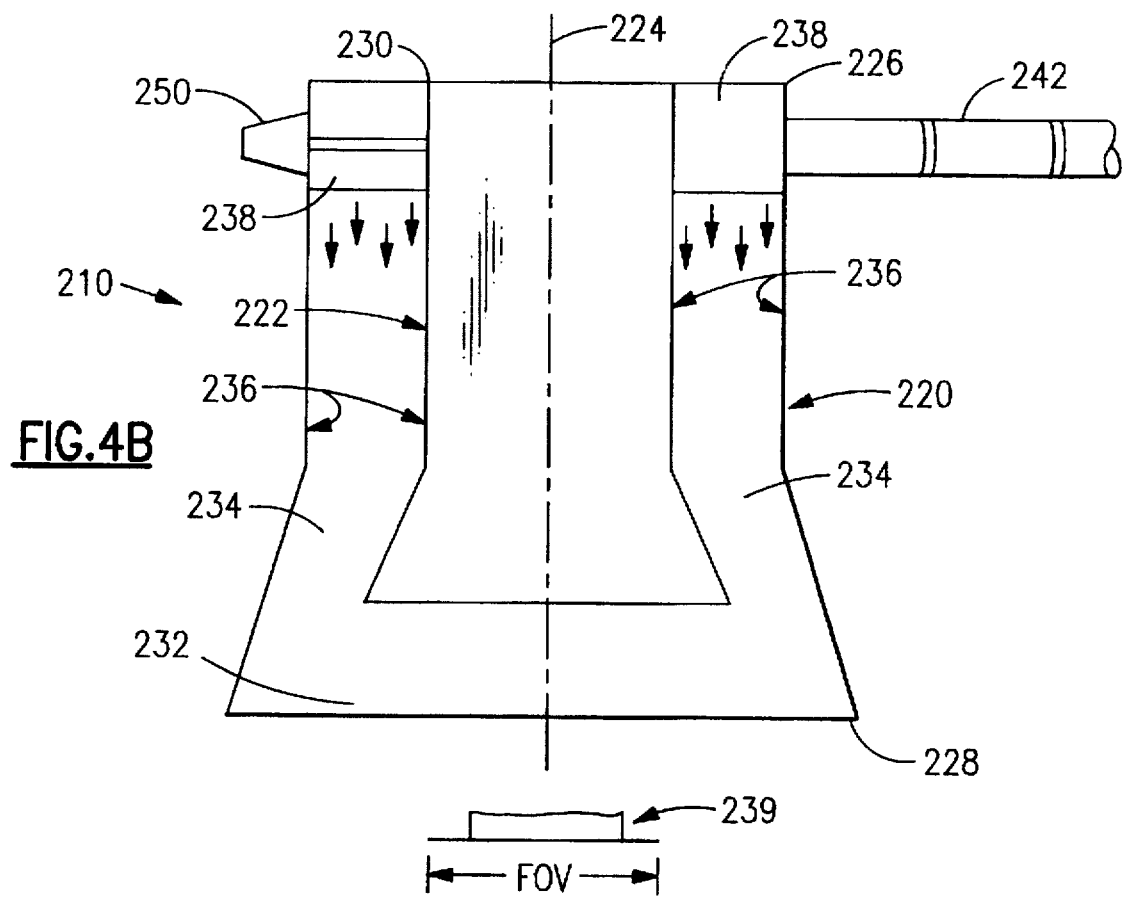
FIG. 4B is a sectional view of the same embodiment.

FIGS. 4A and 4B illustrate another embodiment of a diffuse illuminator device 210. The diffuse illuminator device 210 has an outer baffle 220 with a rectangular cross section. The outer baffle 220 defines an optic axis 224, and has a proximal end 226 and an open distal end 228. As in the embodiment of FIG. 2B, the distal end 228 of the outer baffle 220 is outwardly flanged. An inner baffle 222, coaxially disposed within the outer baffle 220, has an open proximal end 230 and an open distal end 232. The distal end 232 of the inner baffle 222 is also outwardly flanged. An annular illuminator 238 is positioned at the proximal ends 230, 226 of the inner and outer baffles 222, 220 in order to direct a ring of illumination towards a target 239. In this embodiment, the distal end 232 of the inner baffle 222 is flanged to a dimension which is greater than that of the proximal end 226 of the outer baffle 220 so that the shape of the light tunnel restricts direct illumination of the target 239 by the annular illuminator 238. A set screw 250 secures the inner baffle 222 to a predetermined position relative to the optic axis 220. A light conduit 242 is used to introduce light from a remote source into the annular illuminator 238.

Figure 5A:
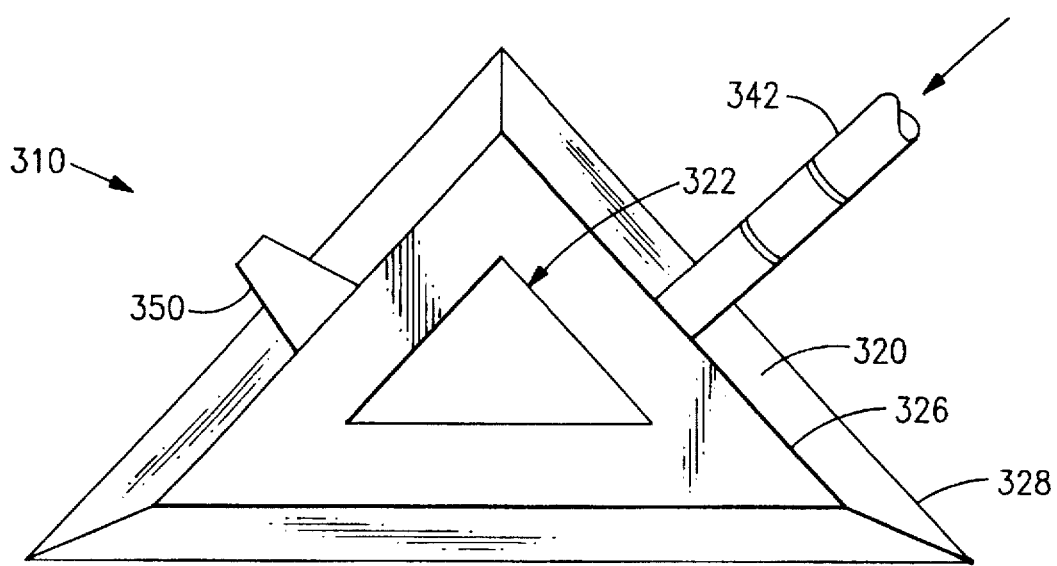
FIG. 5A is a top plan view of another embodiment of this invention in which the cross-sectional area of the outer baffle is triangular.
Figure 5B:
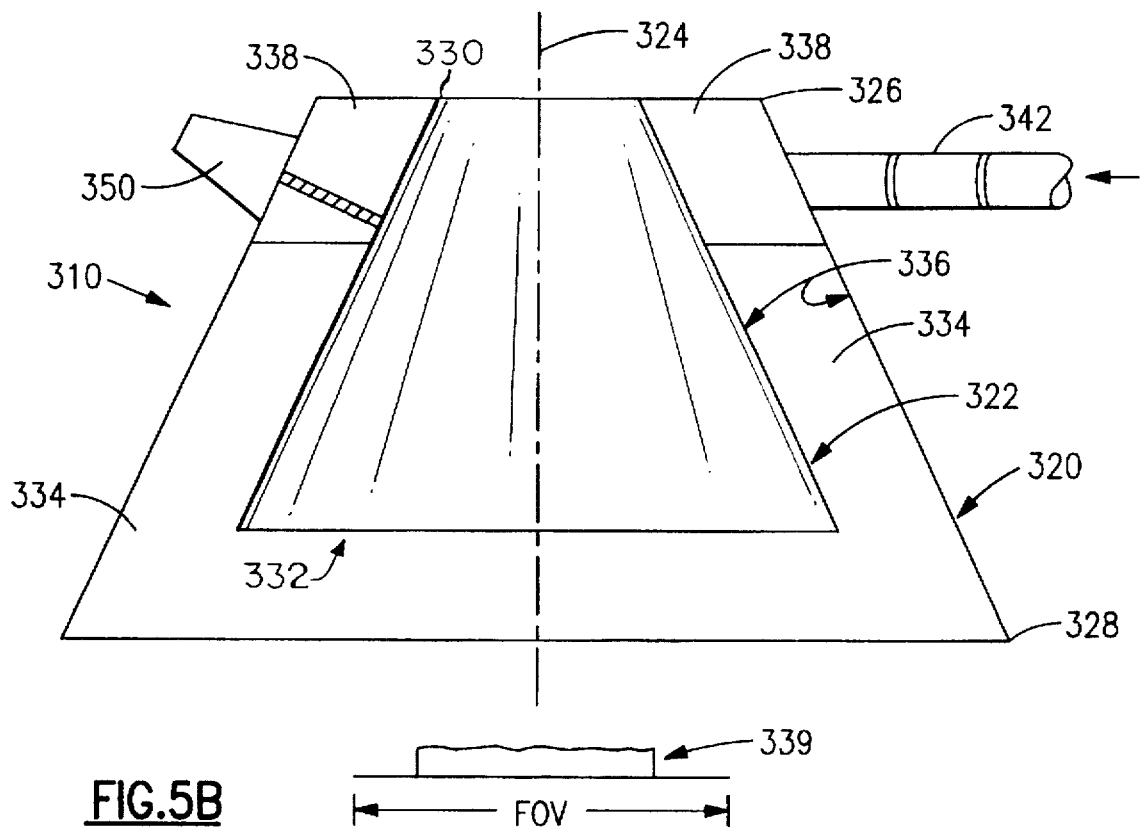
FIG. 5B is a sectional view of the same embodiment.

FIGS. 5A and 5B illustrate another embodiment of a diffuse illuminator device 310. The device 310 has an outer baffle 320 with a triangular cross section. The outer baffle 320 defines an optic axis 324 and has an open proximal end 326 and an open distal end 328. An inner baffle 322, with an open proximal end 330 and an open distal end 332, is coaxially disposed within the outer baffle 320. An annular illuminator 338 is positioned at the proximal ends 330, 326 of the inner and outer baffles 322, 320 to direct a ring of illumination towards a target 339. The inner baffle 322 may be adjusted along the optic axis 324 and secured with a set screw 350. Light from a remote source is introduced into the annular illuminator via a light conduit 342.

Figure 6:
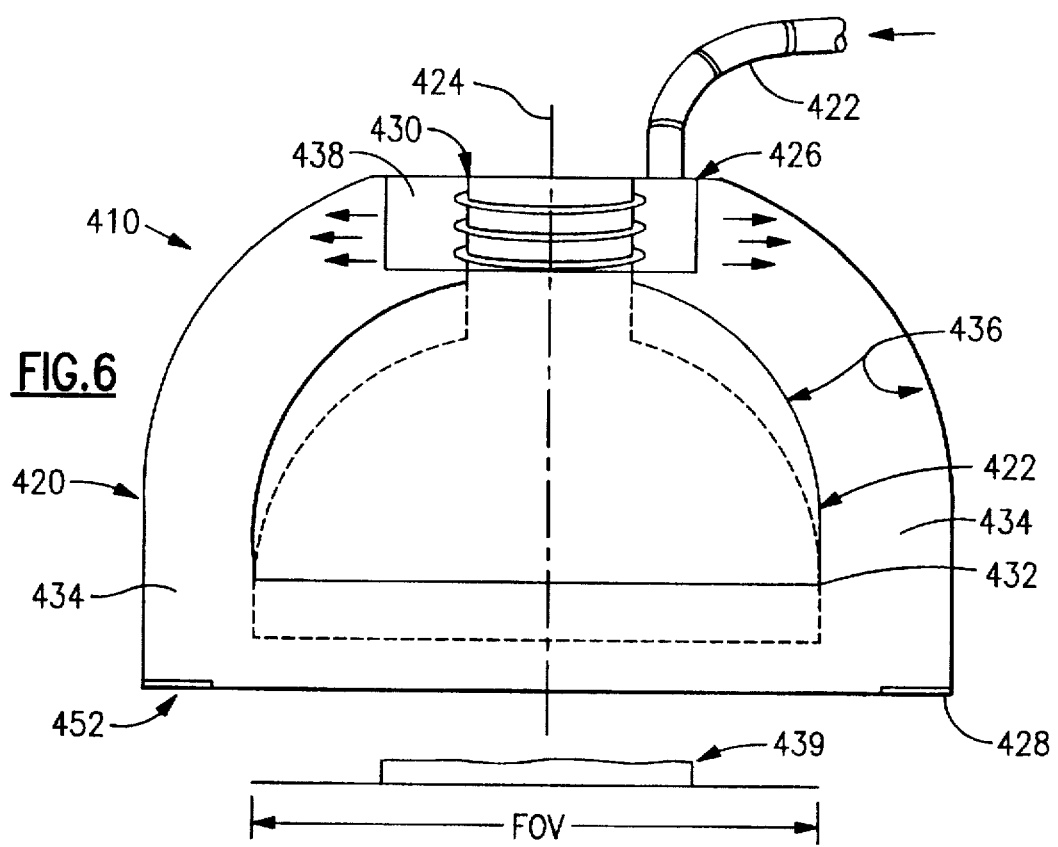
FIG. 6 is a sectional view of another embodiment of this invention in which the inner and outer baffles are hemispherically shaped.

FIG. 6 illustrates another possible embodiment of a diffuse illuminator device 410 according to the invention, this embodiment having a generally hemispherical shape. The device 410 has an outer baffle 420 and a coaxial inner baffle 422. The outer baffle 420 has a proximal end 426 and an open distal end 428 that terminates in an annular lip 452. The baffles 420, 422 define an optic axis 424. The inner baffle 422 terminates in an open, generally tubular proximal end 430. An annular illuminator 438, positioned at the proximal ends 430, 426 of the inner and outer baffles 422, 420 directs a ring of illumination into a light tunnel 434 defined between the two baffles. Light exits the distal end of the light tunnel 434 to illuminate a target 439. Here, the ring illuminator 438 directs the light laterally, or radially, into the light tunnel 434. A light conduit 442 carries light from a remote source to the annular illuminator 438. The proximal portion of the inner baffle 422 can be helically threaded so that the inner baffle 422 may be adjusted along the optic axis 424, as illustrated in phantom lines. As with the foregoing embodiments, adjustment of the axial position of the inner baffle 422 permits adjustment of the illumination structure of light incident on the target 439.

The adjustment of the inner baffle position using a set screw or helical thread are but two of many possible means of adjustment. In other embodiments, a knob or hand-wheel could be used. In further possible embodiments, a stepper motor or other motorized drive could be used, which can be either manually or automatically controlled. The ring illuminator need not direct light axially, but could be configured to direct light radially, as in FIG. 6, or at an angle. Also, rather than an optical fiber device, the illuminator could comprise an array of lamps or LEDs.

While the invention has been described with reference to selected preferred embodiments, it should not be limited to those embodiments. Rather, many modifications and variations will become apparent to those skilled in the art without departure from the scope and spirit of this invention as defined in the appended claims.

I claim:

1. Diffuse illuminator device for providing uniform illumination on a target, comprising:

an outer generally tubular baffle defining an optic axis and having a proximal end and an open distal end;

an inner generally tubular baffle coaxially disposed within said outer baffle, defining an annular light tunnel therebetween, and said inner baffle having an open proximal end and an open distal end;

an annular illuminator positioned at the proximal end of said outer and inner baffles for directing a ring of illumination into said annular light tunnel, and having an open core aligned with the inner baffle open proximal end permitting viewing of said target through said inner baffle; wherein the relative positions of the distal ends of the inner and outer baffles define an illumination structure composed of a mixture of low angle and high angle light incident on the target;

means for adjusting the position of the inner baffle along said optic axis relative to the outer baffle in order to vary the illumination structure; and a beam splitter located near the proximal end of the inner baffle for eliminating reflection of an observer.

2. Diffuse illuminator device for providing uniform illumination on a target, comprising:

an outer baffle defining an optic axis and having a proximal end and an open distal end;

an inner baffle coaxially disposed within said outer baffle, defining an annular light tunnel therebetween, and said inner baffle having an open proximal end and an open distal end;

an annular illuminator positioned at the proximal end of and between said outer and inner baffles for directing a ring of illumination into said annular light tunnel, and having an optically open core permitting viewing of said target through said inner baffle;

a remote light source and a light conduit associated with said light source for conducting light into the annular illuminator;

means within the light tunnel for directing low angle illumination onto the target; and such that illumination incident upon the target is a mixture of low angle illumination and high angle illumination; and means for adjustably moving the inner baffle along said optic axis relative to the outer baffle in order to vary the mixture of low angle and high angle illumination incident upon said target.

3. Diffuse illuminator device as in claim 2 wherein said light conduit contains an optical fiber bundle.

4. Diffuse illuminator device as in claim 2 wherein the outer baffle further contains an inner surface and said means for directing low angle illumination includes an annular reflector attached to the inner surface of the distal end of said outer baffle for directing low angle light onto the target.

5. Diffuse illuminator device as in claim 4 wherein said means for directing low angle illumination further includes at least one diffuse surface in the light tunnel.

6. Diffuse illuminator device as in claim 4 wherein said means for directing low angle illumination further includes at least one specular surface in the light tunnel.

7. Diffuse illuminator device as in claim 4 wherein the inner baffle further contains a diffuse inner surface.

8. Diffuse illuminator device as in claim 4 wherein the inner baffle further contains a light absorbent inner surface.

9. Diffuse illuminator device as in claim 2 wherein the distal end of said outer baffle terminates in an annular lip that extends towards said optic axis for restricting errant light from the target.

10. Diffuse illuminator device as in claim 9 wherein a cross sectional area of said outer baffle is generally elliptical.

11. Diffuse illuminator device as in claim 9 wherein a cross sectional area of said outer baffle is generally rectangular.

12. Diffuse illuminator device as in claim 9 wherein a cross sectional area of said outer baffle is generally triangular.

13. Diffuse illuminator device as in claim 2, wherein the open distal end of said inner baffle is free of any focusing lenses.

14. Diffuse illuminator device as in claim 2, wherein said inner and outer baffles are generally hemispherical in shape.

15. Diffuse illuminator device as in claim 14, wherein said annular illuminator directs said ring of illumination radially into the light tunnel defined between the inner and outer baffles.

16. Diffuse illuminator device for providing uniform illumination on a target, comprising:

an outer baffle defining an optic axis and having an inner surface, a proximal end, and an open distal end;

an annular reflector attached to the inner surface of the distal end of the outer baffle;

an inner baffle coaxially disposed within said outer baffle, defining an annular light tunnel therebetween, and said inner baffle having an open proximal end and an open distal end, said inner baffle defining an optically unobstructed path for viewing the target positioned at the distal end of the outer baffle, wherein the open distal end of said inner baffle is free of any focusing lenses;

an annular illuminator positioned at the proximal end of and between said outer and inner baffles for directing a ring of illumination into said annular light tunnel, and having an optically open core permitting viewing of said target through said inner baffle;

a remote light source;

a light conduit associated with said light source for conducting light to the annular illuminator;

whereby light from said light source is conducted into said annular illuminator via said light conduit and the light is directed into said annular light tunnel and reflected by reflecting means within the light tunnel towards said target at a low angle of incidence, such that illumination incident onto the target is a mixture of light at the low angle of incidence and at a high angle of incidence; and means for adjustably moving the inner baffle relative to the outer baffle to vary the mixture of illumination at the low angle of incidence and illumination at the high angle of incidence upon said target.

17. Diffuse illuminator device for providing uniform illumination on a target, comprising:

an outer baffle defining an optic axis and having a proximal end and an open distal end, said distal end being outwardly flanged;

an inner baffle coaxially disposed at a position within said outer baffle, defining an annular light tunnel therebetween, and said inner baffle having an open proximal end and an open distal end defining an unobstructed optical path to view said target at the distal end of the outer baffle;

an annular illuminator positioned at the proximal end of and between said outer and inner baffles for directing a ring of illumination into said annular light tunnel, and having an open core permitting unobstructed viewing of said target through said inner baffle;

a remote light source and a light conduit associated with said light source for conducting light into the annular illuminator;

wherein the relative positions of distal ends of the inner and outer baffles define an illumination structure composed of low angle and high angle light incident on the target;

means for adjustably moving the inner baffle along said optic axis relative to the outer baffle in order to vary the illumination structure; and means within the light tunnel for directing low angle illumination onto the target.

18. Diffuse illuminator device as in claim 17 wherein the distal end of said inner baffle is outwardly flanged.

19. Diffuse illuminator device as in claim 17 wherein the distal end of the inner baffle is outwardly flanged and has a cross-sectional area that is greater than a cross-sectional area of the proximal end of said outer baffle.

20. Diffuse illuminator device for providing illumination on a target, comprising:

an outer generally tubular baffle defining an optic axis and having a proximal end and an open distal end;

an inner generally tubular baffle coaxially disposed within said outer baffle, defining an annular light tunnel therebetween, and said inner baffle having an open proximal end and an open distal end, said inner baffle also defining an unobstructed optical path for viewing the target at said distal end of the outer baffle;

an annular illuminator positioned at the proximal end of and between said outer and inner baffles for directing a ring of illumination into said annular light tunnel, and having an open core aligned with the inner baffle open proximal end permitting viewing of said target through said inner baffle; wherein the relative positions of the distal ends of the inner and outer baffles define an illumination structure composed of a mixture of low angle and high angle light incident on the target; and means for adjustably moving the inner baffle to adjust the position of the inner baffle along said optic axis relative to the outer baffle in order to vary the illumination structure; wherein said means for adjustably moving the inner baffle along the optic axis includes an adjustment device having a handle disposed outside the outer baffle.

* * * * *